United States Patent
Eck et al.

(10) Patent No.: US 7,822,241 B2
(45) Date of Patent: Oct. 26, 2010

(54) DEVICE AND METHOD FOR COMBINING TWO IMAGES

(75) Inventors: Kai Eck, Aachen (DE); Jörg Bredno, Aachen (DE); Paul Antoon Cyriel Desmedt, Eindhoven (NL); Peter Maria Johannes Rongen, Eindhoven (NL); Herman Stegehuis, Best (NL); Geert Gijsbers, Best (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 739 days.

(21) Appl. No.: 10/568,479

(22) PCT Filed: Aug. 11, 2004

(86) PCT No.: PCT/IB2004/051446

§ 371 (c)(1),
(2), (4) Date: Feb. 15, 2006

(87) PCT Pub. No.: WO2005/020147

PCT Pub. Date: Mar. 3, 2005

(65) Prior Publication Data

US 2006/0262966 A1 Nov. 23, 2006

(30) Foreign Application Priority Data

Aug. 21, 2003 (EP) .................... 03102615

(51) Int. Cl.
*G06K 9/00* (2006.01)
*G06K 9/32* (2006.01)
(52) U.S. Cl. ............ 382/128; 382/284; 382/294
(58) Field of Classification Search ............ 382/128, 382/130, 131, 132, 284, 294; 345/629, 634
See application file for complete search history.

(56) References Cited

U.S. PATENT DOCUMENTS

| 4,869,247 | A | | 9/1989 | Howard, III et al. |
|---|---|---|---|---|
| 5,285,786 | A | * | 2/1994 | Fujii ........................... 600/425 |
| 5,369,678 | A | | 11/1994 | Chiu et al. |
| 5,568,384 | A | * | 10/1996 | Robb et al. .................. 715/202 |

(Continued)

FOREIGN PATENT DOCUMENTS

EP        0606709 A2      7/1994

(Continued)

OTHER PUBLICATIONS

J. B. Antoine Maintz, et al: A Survey of Medical Image Registration, vol. 2, No. 1, 1998, pp. 1-37, XP001032679.

(Continued)

*Primary Examiner*—Jon Chang

(57) ABSTRACT

Images of static vascular maps (B), which were taken at different phases of the cardiac cycle and/or the respiratory cycle and were archived in a memory (6), are superimposed on a current image (A) of a catheter (2, 8) in the vascular system (9). In the method, a defined section of a map image (B) around the estimated actual position of the catheter is selected and is displayed superimposed on the current image (A) on a monitor (10). The map image (B) used for this is preferably selected by an electrocardiogram to match the particular cardiac cycle. The position of the catheter relative to the map image (B) is estimated using a distance image (D).

19 Claims, 1 Drawing Sheet

U.S. PATENT DOCUMENTS

Figure 1:
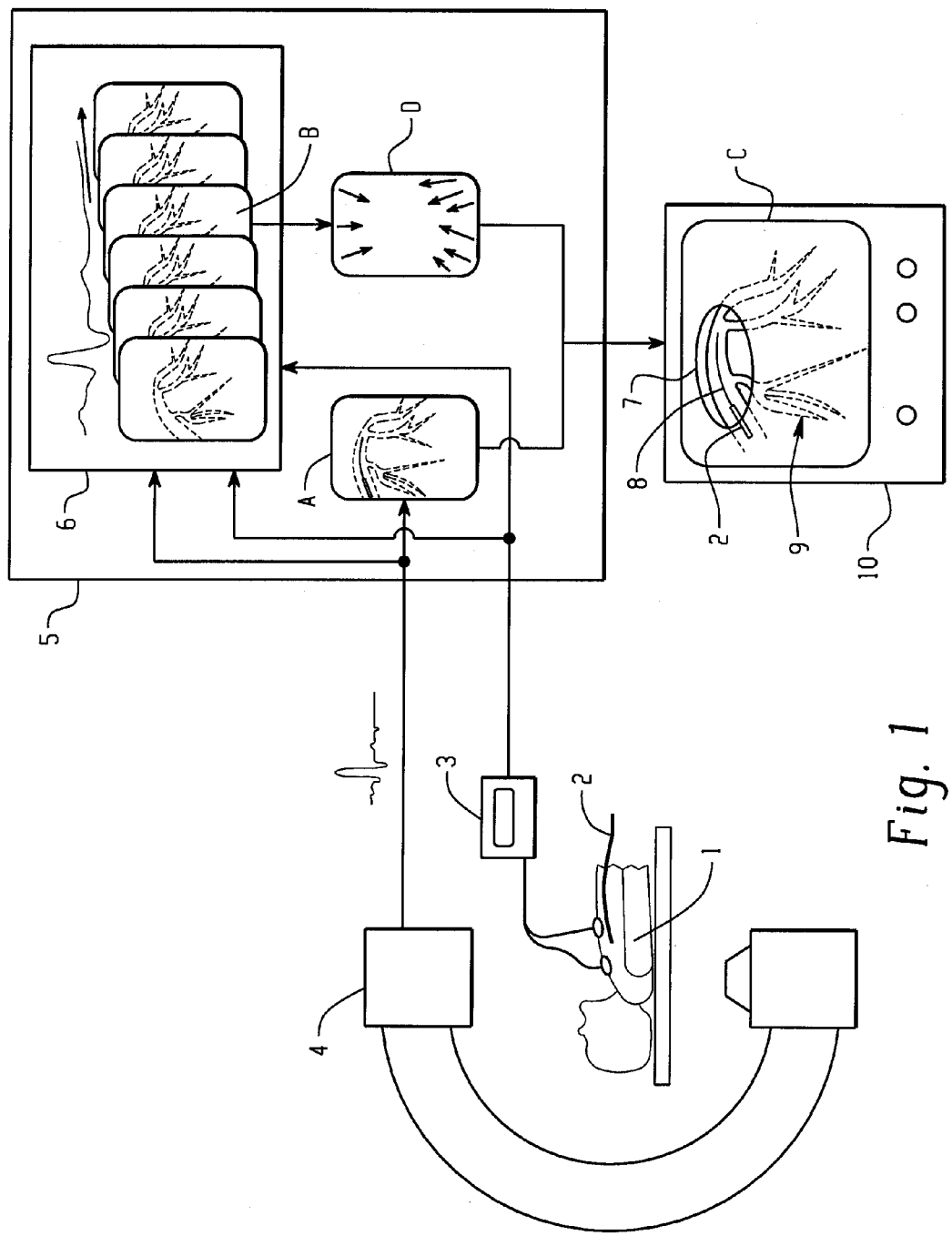

| | | | |
|---|---|---|---|
| 5,690,111 A | | 11/1997 | Tsujhino |
| 5,718,229 A | | 2/1998 | Pesque et al. |
| 5,797,843 A | * | 8/1998 | Fitch et al. .................. 600/437 |
| 6,370,417 B1 | * | 4/2002 | Horbaschek et al. ........ 600/424 |
| 6,556,695 B1 | * | 4/2003 | Packer et al. ................ 382/128 |
| 6,859,548 B2 | * | 2/2005 | Yoshioka et al. ............ 382/128 |
| 7,280,710 B1 | * | 10/2007 | Castro-Pareja et al. ...... 382/303 |
| 2004/0081269 A1 | * | 4/2004 | Pan et al. ....................... 378/4 |

FOREIGN PATENT DOCUMENTS

| | | |
|---|---|---|
| EP | 0952547 A2 | 10/1999 |
| JP | 2002237996 A1 | 8/2002 |
| WO | 0120552 A1 | 3/2001 |
| WO | 0241780 A1 | 5/2002 |

OTHER PUBLICATIONS

Karrien E. et al: Fully Automatic 3D/2D Substracted Angiography Registration, Mar. 1999, pp. 664-671, XP008010055.

Thomas Netsch, et al: Towards Real-Time_Modality 3-D Medical Image Registration, 2001 IEEE, pp. 718-725 XP10554053A.

Y. Bentoutou, et al: An Invariant Approach for Image Registration in Digital Subtraction Angiography, Pattern Recognition 2002, vol. 35, pp. 2853-2865.

* cited by examiner

DEVICE AND METHOD FOR COMBINING TWO IMAGES

The invention relates to a device and to a method for combining a current image of an object and a map image of the dwell region of the object.

The combination of a current image of an object and a map image of the object surroundings is performed, for example when navigating a catheter through the vascular system of a patient. The underlying problem will therefore be explained subsequently considering as example a cardiac catheter examination, although the present invention is not restricted to this area of application. In the case of the systems customarily used for cardiac treatment, static angiograms and fluoroscopic images currently being recorded are displayed on two different monitors side by side. Angiograms are here depictions of the vascular system, in which the vessels are displayed highlighted, for example by administering a contrast medium. In the case of these systems, it is left to the doctor carrying out treatment to relate the position of an object, such as, for example, a catheter or a guide wire, recognizable on the current picture, to the map image of the vascular system, that is, to superimpose in his mind the two monitor images displayed side by side.

In this context, a device is known from JP-A-2002-237996, in which a current fluoroscopic image and a static vascular map are superimposed on the same monitor. The difficulty with such superimpositions is that owing to an overall movement of the patient as well as his heartbeat and breathing, the position and form of organs in the current images constantly change, so that to some extent considerable geometrical and anatomical discrepancies exist between the superimposed images. To alleviate this problem, data banks containing static vascular maps from different phases of the cardiac and/or respiratory cycle can be used in order by means of an electrocardiogram (ECG) and/or the measured respiration phase to allocate a current fluoroscopic image to the static vascular map (from the same or a similar cardiac or respiratory cycle) that is the best match for it. Even when using such advanced methods, geometric discrepancies between the superimposed images still remain, which can seriously impair the optical impression and consequently the usefulness of the superimposition.

Against this background, it is an object of the present invention to provide means for improved combined representation of a current image of an object and a map image of the dwell region of the object.

The device according to the invention is used for combination (e.g. combined display) of an image of an object and a map image of the (especially form-changing) dwell region of the object. The first-mentioned image is referred to hereinafter as the "current image", without a restriction being associated with this in relation to specific periods of time. Neither are there any fundamental restrictions in respect of the dimensions of the current image and the map image (1D, 2D, 3D, 4D,). The object can in general be any object or region to be displayed for the purpose of a "motive". For example, the "object" can be an anatomical structure of interest (organ, bone, tumor etc.), a functionally defined region (e.g. an area with specific activity of metabolism or blood vessel formation), a catheter tip or a guide wire in the vascular system of a patient, or a capsule located in the gastrointestinal tract. The last-mentioned examples pertain to an especially important situation in which the object is located in a path network and is able to move only along the paths allowed by this. In these cases, the map image preferably portrays the path network in highlighted form. For example, the map image can be an angiogram that has been prepared from the vascular system of a patient to whom contrast medium has been administered. The term "map image" is incidentally, however, to be understood quite generally as any collection of information that is or can be assigned to locations in the dwell region of the object. Mathematically, a map image can typically generally be described by a single-valued or multiple-valued function across a one-dimensional or higher-dimensional definition range.

The device contains a data-processing system, which is designed to perform the following steps:

a) To estimate the position of the object of interest is relation to the map image. This means that in the current image the position of the object is established and the position corresponding thereto in the map image is estimated. If the position and form of the dwell region of the object on the current image and on the map image were the same, then it would be possible to determine the corresponding position exactly. In reality, however, the dwell region changes its form and position in an unknown manner, so that the corresponding position has to be estimated. At the same time, it can optionally be considered corrective that the object must inevitably be located in a path network, if this condition applies in the case of the underlying application.

b) The map image is combined with the current image in such a way that the estimated position of the object in the map image coincides with the actual position of the object in the current image; for the combination, only a section of the map image and/or a section of the current image are/is used. The "combination" of the map image and the current image can include in particular an additive superimposition of the images, or alternatively a subtraction, a contour emphasis or any other operation for combining the image contents. In the following, the case in which only a section of the map image is used will be taken as a representative basis (the relevant remarks shall apply correspondingly also to the use of a section of the current image). As a rule, the entire current image is then used in the combination. Limitation to a sub-region of the current image is also possible, however, wherein in that case the sizes of the map image section and sub-region will preferably correspond.

With the device described it is possible to combine a "current" image of an object with a static map image of the dwell region thereof without disruptive global discrepancies between the two images occurring. This is achieved in that from the map image (or the current image) only a section around the object of interest is used for the combination. Such a—comparatively small—section can be allocated with great accuracy and geometrically correctly to the actual position of the object, since during the image registration the coincidence between current image and map image does not have to be oriented to a global (mean) dimension. Using the device, in particular also a satisfactory, geometrically correct superimposition is therefore possible in the case of path networks, such as the vascular system of a patient for example, which have an inherent deformability that can be described only with difficulty or only with unsatisfactory accuracy by mathematical transformations. Restriction of the combination to a local section can advantageously be used irrespective of the specifically used method of image registration (rigid, non-rigid, unimodal, multimodal etc.) and in many cases allows the use of new or known algorithms that were not suitable for a global registration. A further advantage of the restriction lies in the fact that as a rule the image registration is clearly less costly as regards its time and memory requirement.

In an optional embodiment of the invention, the map image can contain additional information about structures and/or functions of the dwell region of the object. For example, it can reproduce the (assumed) position of organs, the intensity of blood vessel formation and/or the metabolic activity in the dwell region of the object. In that respect there is a virtually unlimited number of applications in which the "multimodal" registration of information from different sources is desired and helpful for the user. The combination of CT pictures of part of the skeleton with NMR (magnetic resonance) pictures of the tissue in the associated region of the bones and the joints can be mentioned as representative of this. According to the proposed method, in this case a section of a NMR image can be brought locally into register with a CT image or conversely a section of a CT image can be brought into register with a NMR image. The object forming the basis of the registration can in this case be, for example a swelling of the tissue that is on the one hand a typical indication of a fracture, but on the other hand does not show up on X-ray images. In the case of those fractures that cannot readily be identified on an X-ray image, using the proposed method the site of the swelling observable on the NMR image can be localized on the X-ray image and the region that is to be examined with greatest attention for a fracture can be indicated on the X-ray image.

The device can in particular contain a monitor linked to the data-processing arrangement, on which the combination of the current image and the map image (or the corresponding sections) is displayed. In the context of a catheter investigation, for example, a doctor can then observe on the monitor fluoroscopic live images of the catheter, which at the same time show him the vascular structure around the catheter as a section of a vascular map.

According to a further aspect of the device, this contains a memory for storing a number of map images, the map images being categorized according to a varying state of the dwell region of the object. In this instance it is possible to select from among the several map images an optimum map image for the combination to be effected.

The device contains furthermore preferably a sensor device for detecting at least one parameter that describes a varying state of the dwell region of the object. In particular, the sensor device can be designed to detect an electrocardiogram and/or the respiratory cycle of a patent undergoing examination. Such a sensor device can be used in conjunction with the above-mentioned memory for a number of map images, in order on the one hand to categorize the stored map images according to the associated state of the path network and in order on the other hand to determine the state of the dwell region pertaining to the current image.

In conjunction with the above-mentioned embodiment of the device containing a memory, the data-processing system can furthermore be arranged to select from the memory of the device those map images of which the "index" or associated state of the dwell region of the object is the best match for the state of the said dwell region that existed as the current image was being taken. If, for example, the memory contains several map images of the vascular system of a patient at different phases of the cardiac cycle, one can select from these the one that comes from the same phase of the cardiac cycle as the current image. In this manner it is possible to take into account parameterizable and especially cyclical spontaneous movements of the path network and from the outset to combine the current image only with a map image that is the best possible match.

There are various options for estimating the correspondent position of the object in a map image within the framework of an image registration of current image and map image. In particular, with the existence of a spatially-defined structure, such as an organ or a path network, for example, the data-processing system can be arranged to assign to each pixel in a map image a probability that it will belong to the structure (e.g. to the path network). In many cases of application, it is in fact impossible to distinguish reliably between pixels that belong to a structure and those that do not belong to it. In such cases, when using the map image a probability-based segmentation allows the highest possible probability for the accuracy of the result to be sought and the reliability of the result to be quantified.

Furthermore, the data-processing system can be arranged to produce a distance, image from the map image by a distance transformation. A distance transformation is an operation known from digital image-processing (cf. Jähne, Digital Bildverarbeitung, $5^{th}$ edition, Chapter 18, Springer Verlag Berlin Heidelberg, 2002). Here, a pixel of the distance image can in particular contain information about in which direction and/or at what spacing from that point there is a greater probability for the existence of a specific segmentation object. The distance image is therefore well suited for estimating the position of an object relative to the map image. For example, a roughly estimated starting position of a catheter on the map image can be converted by means of the distance information into a position of the catheter that lies with greater probability in the vascular system (path network). Distance images can advantageously be calculated in advance from the existing map images, so that they are ready and available during the processing of a current image. This allows an error-tolerant estimation of the position of the object in real time. Superimposition of map image and current image can therefore be carried out so quickly and so accurately that it represents real assistance for the eye-hand co-ordination of the doctor.

Depending on the application, the section that is used from the current image and/or the map image can be of different size and of different form. In particular, it can be rectangular or oval. Typically, the size (area, volume) of the section amounts to about 5% to 50%, preferably about 10% to 30%, of the size of the map image or current image. According to an optional embodiment of the device, the section contains only the separate representation of a spatially-defined structure, such as a path network for example. All points that do not lie on the structure are then transparent in the section. In that way, the section accentuates only the said structure around the object of interest, without concealing other image information of the current image.

The device can contain in particular an imaging means, such as an X-ray apparatus, for example, and/or an NMR apparatus, with which the current image of the object can be produced. Furthermore, the imaging means can be used to produce the map images of the dwell region of the object as well. Such a device is especially suitable for navigating a catheter in the case of surgical treatment. The device can in particular contain more than one imaging means, for example, an X-ray apparatus and an NMR apparatus, so that the current image and the map image(s) can originate from different modalities.

The invention relates furthermore to a device and to a method for combined portrayal of a current image of an object that is located in a path network and a map image of the path network. The device contains a data-processing system that is arranged to execute the said method, the method comprising the following steps:

a) in the map image, to assign to each pixel a probability that it belongs to the path network;
b) to produce a distance image from the map image by a distance transformation;

c) by means of the distance image to estimate the position of the object in relation to the map image of the path network, and d) to superimpose the map image wholly or partially on the current image or a section thereof so that the estimated-position of the object in the map image is brought into register with the actual position of the object in the current image.

When in step d) only a section of the map image and/or of the current image are/is used, the device corresponds to a variant of the above-defined device For a more detailed explanation, the reader can therefore be referred largely to the above description. According to an independent aspect of the invention, the above-defined device nevertheless also includes the case in which a different section of the map image or the entire map image is superimposed on the current image. The advantage of the device in this regard lies in enabling an error-tolerant superimposition in real time with a probability-based segmentation and a distance imaging, which significantly increases the value of the superimposition, for example, within the scope of a monitor display.

Finally, the invention also relates to a method for combining a current image of an object and a map image of the dwell region of the object. The method here contains the following steps:

a) estimation of the position of the object in relation to the map image, b) combination of the map image around the estimated position of the object with the current image, the estimated position of the object in the map image being brought into register with the actual position of the object in the current image, and only a section of the map image and/or of the current image being used.

The method implements in general form the steps that can be performed with a device of the kind described above. As regards the definition of terms, advantages and further aspects of the method, the reader is therefore referred to the above description of the device.

These and other aspects of the invention are apparent from and will be elucidated, by way of non-limitative example, with reference to the embodiments described hereinafter.

The single FIGURE shows schematically the components of a device according to the invention for superimposed representation of two images.

In the case of the medical application illustrated in the FIGURE as a representative example, the movement of a catheter 2 or more precisely of the catheter tip and/or a guide wire 8 in the vascular system 9 of a patient 1 is to be observed. For that purpose, fluoroscopic X-rays images of the body volume being examined are produced with an X-ray apparatus 4, and are transferred as current images A to a data-processing system 5. The difficulty with such fluoroscopic images is that the vascular system 9 stands out only faintly thereon, so that with this system reliable navigation of the catheter or a guide wire to a specific location within the vascular system is hardly possible. A better portrayal of the vascular system could, admittedly, be achieved by injection of a contrast medium, but such measures must be used as sparingly as possible, owing to the stress associated therewith for the patient.

To improve catheter navigation, in the case of the system illustrated several angiograms B are prepared with the X-ray apparatus 4 before or during the actual catheter examination 4 and are stored in a memory 6 of the data-processing system 5. The angiograms can be produced, for example, by injections of contrast medium, so that the vascular tree of the patient can easily be seen on them. They are therefore hereinafter referred to also as "map images" or "vascular maps" (road maps).

Since the heartbeat has significant effects on the position and form of the vascular system of the heart and the adjoining organs, map images B from different phases of the cardiac cycle of the patient 1 are archived in the memory. The cardiac phase belonging to a particular map image B is here indicated by an electrocardiogram, which is recorded by an electrocardiograph 3 in parallel with the X-ray images. Furthermore, map images can be prepared also at different phases of the respiratory cycle, which is detected by a respiration sensor such as a chest belt or similar. For the sake of clarity, such an additional or alternative indication of the map images B by way of the respiratory cycle is not specifically shown in the FIGURE.

During the catheter examination carried out for therapeutic or diagnostic purposes, fluoroscopic images A of the catheter tip or a guide wire 8 are continuously produced and passed together with the associated ECG to the data-processing system 5. The phase of the electrocardiogram or of the cardiac cycle pertaining to a current image A is then established by the data-processing system 5, and the map image B that matches this cardiac phase best is selected from the memory 6.

The current image A and the map image B can in principle be displayed side by side on two different monitors or superimposed on one another on the same monitor. Since the map image B to the matching cardiac phase was selected, the geometrical or anatomical correspondence between the images A, B thus superimposed would already be a comparatively good one. Nevertheless, because of parallax in the image production, because of soft tissue movement and as a result of similar influences, in practice slight discrepancies always appear between the superimposed aggregate images, and cannot be eliminated by global transformations. These discrepancies can be visually very disruptive and considerably diminish the use of the superimposition.

To avoid the above-described problems in the complete superimposition of a current image A and a map image B, it is proposed in the combined portrayal C to use just one more or less small section 7 of the map image B for the superimposition, which just covers the region of interest around the catheter tip or the guide wire 8. Typically, the area of the section 7 amounts to about 25% of the area of the map image B. In such a limited region, the positioning or registering of the section 7 can be carried out with greater accuracy than with a global registering of two images A. B. Moreover, all bothersome inconsistencies between the two superimposed images outside the region 7 are omitted. In the superimposed portrayal C, the current image A therefore remains largely unchanged, whilst in the overlap region 7 even relatively small shifts, which are created, for example, by parallax or patient movements, can be compensated for with good accuracy.

The preceding and following remarks naturally apply analogously also in the case of an equivalent embodiment of the method, in which a section of the current image A is superimposed on a map image B (or a part thereof).

In a preferred algorithm for superimposing a section 7 of the map image B on a current image A, in the map images B the vascular tree is roughly pre-segmented. Segmentation in image processing is understood to mean the assignment of pixels to objects. Since in the case of real X-ray images of the vascular system it is not normally possible to assign a pixel reliably to a vessel, a probability-based segmentation is preferably effected here. In this, each pixel is assigned a value that describes the probability that the pixel belongs to a vessel. Furthermore, for each such map image a distance image D is produced by means of a distance transformation. The value of a pixel of the distance image indicates in what direction from or at what distance from the point under consideration there is a greater probability of the presence of a vessel. The probability-based map image B can be rendered visible, for example, by a height relief across an image area, in which the highest points of the relief have the greatest probability of belonging to the vascular system. The associated distance image can then be defined as the gradient field of the relief, wherein each gradient vector points in the direction of the most direct route to a vessel. The calculation of the probability-based map images B and the associated distance images D can advantageously be effected off-line or in advance, the results being held in the memory 6. During the medical examination, these calculations therefore do not impede implementation of the method.

After selecting from the memory 6 the map image B that best matches the current image A, the distance image D pertaining to this map image B is used to estimate the position of the object of interest (catheter or guide wire) on the map image B. For that purpose, first of all, the (radio-opaque) object in the current image A is segmented. The map image B is then brought into register with the segmented object using the distances of all object pixels out of the distance image D. At the same time, only a rigid displacement (shift and/or rotation) of the segmented object relative to the map image B is permitted.

As a result of the described registration, the best possible estimated position of the catheter or the guide wire 8 relative to the map image B is known. Using this information, depending on the application, a section 7 from the map image B can then be fixed around the estimated position of the object. On a monitor 10, this section 7 is finally superimposed on the current image A in a combination image C, the estimated position of the object in section 7 being brought into register with the actual position of the object (e.g. the guide wire 8) on the current image A. The geometrical discrepancy between the superimposed structures is extremely small in the combination image C.

The form of the section 7 can in principle be selected as desired. Apart from the elliptical form illustrated in the FIGURE, alternatively a rectangular form or any desired different form could be selected. Moreover, the section 7 could contain merely the vessel itself, and otherwise be transparent. Furthermore, a digital contrast enhancement is preferably carried out within the region 7, in order to improve the recognizability of the guide wire 8.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An image processing device for combining a current image of an object and a map image of a dwell region of the object, comprising:
   a memory for storing a number of map images which are categorized according to a varying state of the dwell region of the object;
   a monitor for displaying a combination of the current image and a section of the map image, wherein the current image and the map image are from different imaging source; and
   a data processor arranged:
     a) to select one of the map images most closely categorized by a current state of the dwell region in which the current image is generated,
     b) to estimate the position of the object in the current image in relation to a section of the map image most closely categorized by the current state, the section of the map image most closely categorized by the current state of the dwell region just covering a region around the estimated position of the object, and
     c) to combine the section of the map image most closely categorized by the current state of the dwell region around the estimated position of the object in the current image, the estimated position of the object in the section of the map image most closely categorized by the current state of the dwell region being brought into registration with the actual position of the object in the current image;
   such that the monitor displays the current image with the section of the map image most closely categorized by the current state of the dwell region which just covers the region around the object combined with the corresponding region of the current image.

2. The device of claim 1, wherein the data processor is arranged to produce a distance image from the map image most closely categorized by the current state of the dwell region, each pixel of the distance image being assigned a vector which indicates a direction or distance therefrom has a greater probability of the presence of a preselected spatially-defined structure.

3. The device of claim 2, wherein the data processor is arranged:
   to assign to each pixel in the section of the map image most closely categorized by the current state of the dwell region to each pixel a probability that it belongs to the spatially-defined structure.

4. The device of claim 1, wherein the map images represent at least blood vessels of a patient, the object is at least a portion of a catheter or guide wire, and the current image represents at least the portion of the catheter or guide wire moving through the blood vessels of the patient, and wherein the processor is arranged to estimate the position of the portion of the catheter or guide wire in the current image in relation to the section of the map image most closely categorized by the current state of the dwell region by:
   a) segmenting the portion of the catheter or guide wire in the current image;
   b) registering the section of the map image categorized by the current state of the dwell region using the distances of a distance image whose pixels indicate a direction or distance in which a blood vessel is most probably located;
   c) rigidly displacing the segmented portion of the catheter or guide wire relative to the section of the map image which is most closely categorized by the current state of the dwell region.

5. The device of claim 4, wherein the data processor is arranged to combine the section of the map image most closely categorized by the current state of the dwell region with the current image including:
   a) superimposing the section of the map image on the current image with the estimated position of the portion of the catheter or guide wire registered with the actual position of the portion of the catheter or guide wire in the current image.

6. The device of claim 5, wherein the processor is further arranged to:
carry out a digital contrast enhancement within the section of the map image to improve recognizeability of the portion of the catheter or guide wire.

7. The device of claim 5, wherein the superimposed region of the map image contains blood vessels and other than the blood vessels is transparent.

8. A data-processing system for combining each of a plurality of current images of a patient and a corresponding map image of a region of the patient in a state most closely corresponding to a current state, wherein the current image and the map image are from different imaging sources, the system comprising a data processor arranged for:
receiving one of the current images of the patient in depicting an object which is moving in the patient;
retrieving the corresponding map image from a memory which stores map images corresponding to each of a plurality of the states of the region of the patient;
estimating the position of the object depicted in the received current image in the corresponding map image;
registering the estimated position of the object with a position of the object in the received current image; and
combining at least a section of the corresponding map image around the estimated position of the object with the current image with the estimated position of the object in the corresponding map image superimposed on the actual position of the object in the received current image.

9. The data processing system of claim 8, wherein the object is moved in a path network and the map images depicts the path network.

10. The data processing system of claim 8, wherein one of the different imaging sources provides an image showing the position of an organ, an image showing the formation of a blood vessel, or an image showing metabolic activity.

11. The data-processing system of claim 8, wherein the data processor is arranged to combine only a section of the corresponding map image which surrounds the estimated position of the object with the received current image.

12. The system of claim 11, wherein the section of the corresponding map image contains only the path network and is otherwise transparent.

13. The data-processing system of claim 8, wherein the data processor is arranged to:
assign to each pixel in the map image a probability that it belongs to a spatially-defined structure of the patient; and
produce a distance image from the map image by a distance transformation, each pixel of the distance image defining a vector that points in a direction of a most direct route to the spatially-defined structure.

14. The system of claim 8, wherein the data processor is arranged to register the estimated position of the object with the position of the object in the received current image using a distance image, each pixel of the distance image including a gradient vector which points in a direction of the a direct route to a spatially-defined structure of the patient.

15. The system of claim 14, wherein the data processor is arranged to segment the object in the current image using a probability based segmentation in which each pixel is assigned a probability that the pixel belongs to the spatially-defined structure of the patient.

16. A method for combining the map images that represent at least blood vessels of a patient and a current image that represents at least a portion of a catheter or guide wire, and the current image represents at least the portion of the catheter or guide wire moving through the blood vessels of the patient, the current image and the map images being from different imaging sources, the method comprising with a processor, performing the following steps:
A) estimating a position of the portion of the catheter or guidewire including:
a) segmenting the portion of the catheter or guide wire in the current image;
b) registering the section of the map image categorized by the current state using the distances of a distance image whose pixels indicate a direction or distance in which a blood vessel is most probably located;
c) rigidly displacing the segmented portion of the catheter or guide wire relative to the section of the map image which is most closely categorized by the current state; and
B) combining the map image around the estimated position of the portion of the catheter or guidewire with the current image, the estimated position of the portion of the catheter or guidewire in the map image being brought into register with the actual position of the portion of the catheter or guidewire in the current image, using at least a section of the map image which covers the region around the portion of the catheter or guidewire.

17. The method of claim 16, wherein in the step of combining at least the section of the map image with the current image, only the section of map image which just covers the region around the portion of the catheter or guide wire is combined with just a section of the current image which just covers the region around the portion of the catheter or guide wire; and further comprising:
C) generating a display of the current image with just the region around the portion of the catheter or guide wire being a combination of corresponding sections of the map image and the current image.

18. The method of claim 16, wherein combining the map image around the estimated position includes:
a) segmenting the portion of the catheter or guide wire in the current image.

19. A non-tansitory computer-readable medium carrying instruction for controlling a processor to perform the method of claim 16.

* * * * *